United States Patent
Okamoto et al.

(10) Patent No.: US 10,605,763 B2
(45) Date of Patent: Mar. 31, 2020

(54) METHOD OF REDUCING OUTPUT DEGRADATION OF GAS SENSOR

(71) Applicant: NGK INSULATORS, LTD., Nagoya-shi, Aichi (JP)

(72) Inventors: Taku Okamoto, Nagoya (JP); Noriko Hirata, Nagoya (JP); Yuki Nakayama, Nagoya (JP)

(73) Assignee: NGK Insulators, Ltd., Nagoya (JP)

(*) Notice: Subject to any disclaimer, the term of this patent is extended or adjusted under 35 U.S.C. 154(b) by 49 days.

(21) Appl. No.: 15/795,463

(22) Filed: Oct. 27, 2017

(65) Prior Publication Data
US 2018/0128771 A1 May 10, 2018

(30) Foreign Application Priority Data

Nov. 9, 2016 (JP) .................................. 2016-218701

(51) Int. Cl.
| | |
|---|---|
| *G01N 27/406* | (2006.01) |
| *F01N 11/00* | (2006.01) |
| *G01N 27/407* | (2006.01) |
| *F01N 13/00* | (2010.01) |

(52) U.S. Cl.
CPC ......... *G01N 27/4067* (2013.01); *F01N 11/00* (2013.01); *F01N 13/008* (2013.01); *G01N 27/4071* (2013.01); *G01N 27/4075* (2013.01); *F01N 2550/00* (2013.01); *F01N 2560/02* (2013.01); *F01N 2560/20* (2013.01); *Y02T 10/47* (2013.01)

(58) Field of Classification Search
CPC .. G01N 27/407; F01N 11/007; F01N 2570/00
See application file for complete search history.

(56) References Cited

U.S. PATENT DOCUMENTS

| | | | |
|---|---|---|---|
| 8,721,854 B2 | 5/2014 | Aoki et al. | |
| 2001/0045118 A1* | 11/2001 | Lloyd | H01M 8/0247 |
| | | | 73/1.06 |

(Continued)

FOREIGN PATENT DOCUMENTS

| | | |
|---|---|---|
| JP | 06-265522 A | 9/1994 |
| JP | 11-326266 A | 11/1999 |
| JP | 3855979 B2 | 12/2006 |

OTHER PUBLICATIONS

D. Haaland, Noncatalytic Electrodes for Solid-Electrolyte Oxygen Sensors, 127 Journal of Electrochemical Society: Electrochemical Science and Technology, 1980, p. 797-804. (Year: 1980).*

(Continued)

*Primary Examiner* — Luan V Van
*Assistant Examiner* — Caitlyn Mingyun Sun
(74) *Attorney, Agent, or Firm* — Mattingly & Malur, PC

(57) ABSTRACT

A gas sensor includes a sensor element made of an oxygen-ion conductive solid electrolyte, at least one electrode provided to the sensor element so as to contact a measurement gas, and a controller configured to control the gas sensor. The sensor element is heated, by a heater provided to the sensor element, at a temperature higher than an operating temperature set in advance for a predetermined time period at start of the gas sensor, and then the temperature of the sensor element is decreased to the operating temperature.

3 Claims, 5 Drawing Sheets

(56) References Cited

U.S. PATENT DOCUMENTS

| | | | |
|---|---|---|---|
| 2005/0063873 A1* | 3/2005 | Morris | G01N 33/0031 |
| | | | 422/88 |
| 2006/0070890 A1* | 4/2006 | Itoh | G01N 27/4075 |
| | | | 205/775 |
| 2009/0051373 A1* | 2/2009 | Kato | G01N 27/4065 |
| | | | 324/693 |
| 2016/0061768 A1* | 3/2016 | Nakasone | G01N 27/301 |
| | | | 204/412 |
| 2017/0059510 A1* | 3/2017 | Nakasone | G01N 27/4067 |

OTHER PUBLICATIONS

F. Garzon et al. Solid-state mixed potential gas sensors: theory, experiments and challenges, 136-137 Solid State Ionics 2000, p. 633-38. (Year: 2000).*

Dr. Lothar Mussmann, et al., "NSC/SDPF System as Sustainable Solution for EU6b and Up-coming Legislation", 23rd Aachen Colloquium Automobile and Engine Technology 2014, p. 1025-1044.

* cited by examiner

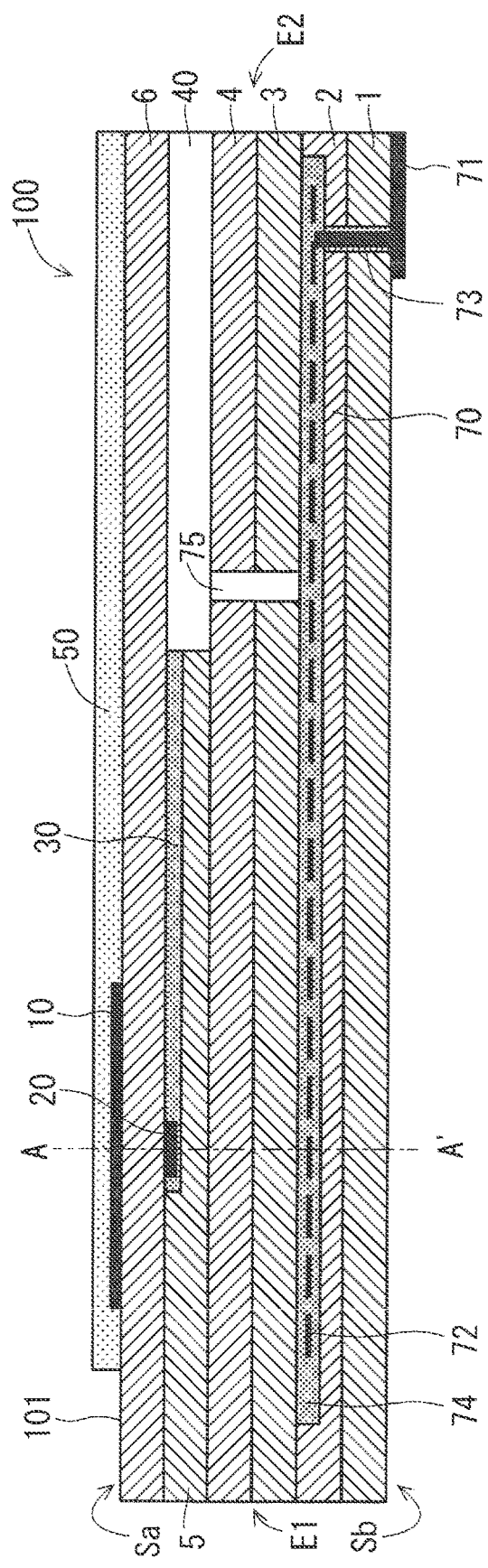
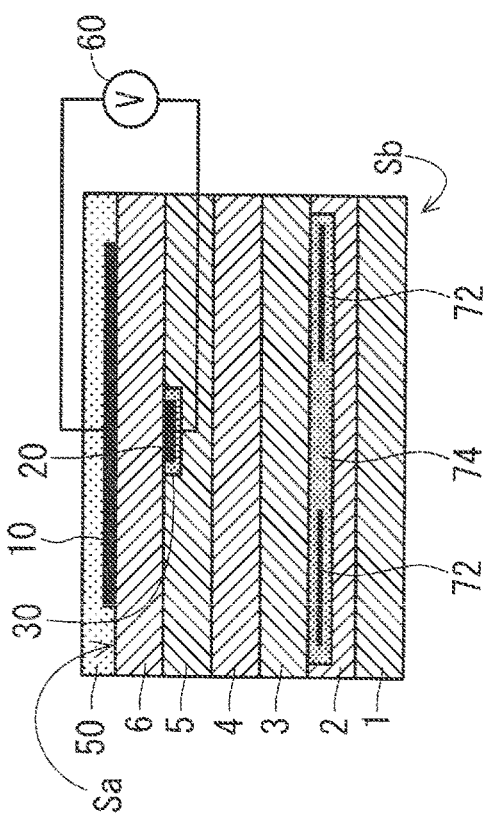
FIG. 2A
FIG. 2B

METHOD OF REDUCING OUTPUT DEGRADATION OF GAS SENSOR

BACKGROUND OF THE INVENTION

Field of the Invention

The present invention relates to a method of reducing output degradation of a gas sensor, and particularly relates to reduction of output degradation attributable to adhesion of a gas component to an electrode.

Description of the Background Art

Gas sensors that sense a predetermined gas component in a measurement gas such as an exhaust gas, for example, to determine its concentration come in various types such as a semiconductor gas sensor, a catalytic combustion gas sensor, an oxygen-concentration difference sensing gas sensor, a limiting current gas sensor, and a mixed-potential gas sensor. Some of these gas sensors, which are obtained by providing electrodes containing a noble metal or a metal oxide as its main constituent to a sensor element mainly made of ceramic being a solid electrolyte such as zirconia, are widely known.

As is also well-known, in a gas sensor which includes a sensor element mainly made of ceramic such as zirconia, a gas component in a measurement gas or a poisoning substance is adhered to the surface of the electrode due to long-term use, or a constituent material of the electrode is sintered due to exposure of the electrode to a high-temperature atmosphere, so that an output value may vary in spite that a concentration of a gas component to be measured in a measurement gas is constant.

Among the above-stated causes for output change of a gas sensor, adhesion of a poisoning substance and sintering of a constituting material of the electrode are irreversible phenomena, and it is considered to be difficult to cope directly with change in output value due to electrode deterioration (irreversible deterioration) caused by those phenomena.

On the other hand, it is possible to cope with output change due to adhesion (adsorption) of a gas component in a measurement gas to the surface of the electrode, by carrying out a predetermined recovery process and removing the adsorbed gas component. That is, such output change is caused due to electrode deterioration (reversible deterioration) caused by a reversible factor. With regard to a gas sensor subjected to such reversible deterioration, execution of a recovery process would allow an original (initial) output value to be re-attained, or would allow an output value as close to the original output value as possible to be obtained.

Examples of the foregoing recovery process include an electrical process (for example, refer to Japanese Patent Application Laid-Open No. 6-265522 (1994) and Japanese Patent No. 3855979), and a heating process (for example, refer to Japanese Patent Application Laid-Open No. 11-326266 (1999)).

The electrical process is a method for recovery output by alternately applying positive and negative potentials between electrodes that are paired through a solid electrolyte, so as to refine the electrode or to desorb an absorbed substance.

On the other hand, the heating process is a method for recovery output with exposure of an adsorbed substance or a poisoning substance to a high temperature to desorb or burn (oxidize) the substance.

It is already publicly known that, in an engine system including an oxidation catalyst halfway through an exhaust pipe connected with an engine, an exhaust gas externally discharged through the exhaust pipe contains a large fraction of a hydrocarbon gas at what is called cold start before the oxidation catalyst activates (refer to "NSC/SDPF System as Sustainable Solution for EU6b and Up-coming Legislation", L. Mussmann et al, 23rd Aachen Colloquium Automobile and Engine Technology 2014, P.1025, for example).

The recovery process can be performed at an optional timing. Thus, at any time when the recovery process becomes necessary in actual use of the gas sensor, the output recovery can be performed. However, in this case, the output of the gas sensor is unavailable during the recovery process.

The inventor of the present invention has researched improvement of the measurement accuracy of a gas sensor to eventually find that adsorption of a gas component in a measurement gas to the surface of an electrode is likely to occur at lower operating temperature of a sensor element. Typically, a gas sensor provided to an engine system and configured to sense, as a measurement gas, an exhaust gas from an engine is driven for use at "key-on" (start) of the engine. Totally considering the above-described finding by the inventor of the present invention and the publicly known fact disclosed in Mussmann et al. that an exhaust gas at cold start contains a larger fraction of a hydrocarbon gas, the gas sensor has been conventionally used while a hydrocarbon gas component is certainly adsorbed to the electrode, in other words, while the measurement accuracy is degraded.

SUMMARY OF THE INVENTION

The present invention relates to a method of reducing output degradation of a gas sensor, and particularly, is directed to a method of reducing output degradation attributable to adhesion of a gas component to an electrode.

According to the present invention, a gas sensor includes: a sensor element made of an oxygen-ion conductive solid electrolyte; at least one electrode provided to the sensor element so as to contact a measurement gas; a heater provided to the sensor element and configured to heat the sensor element; and a controller configured to control the gas sensor, and a method of reducing output degradation of the gas sensor includes the steps of: a) heating, by the heater, the sensor element at a temperature higher than an operating temperature set in advance for a predetermined time period at start of the gas sensor; and b) decreasing, to the operating temperature, the temperature of the sensor element heated to the temperature higher than the operating temperature.

The present invention can excellently reduce temporal output degradation of a gas sensor, which is attributable to adsorption of a gas component in a measurement gas to an electrode, without an unavailable time of the gas sensor.

Thus, the present invention is intended to provide a method capable of reducing degradation of the measurement accuracy of a gas sensor, which is attributable to material adsorption to an electrode, without an unavailable time of the gas sensor.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 2A and 2B are each a diagram schematically illustrating the configuration of a sensor element 101 as a main component of a gas sensor 100;

DESCRIPTION OF THE PREFERRED EMBODIMENTS

<Outline of Engine System and Gas Sensor>

Figure 1:
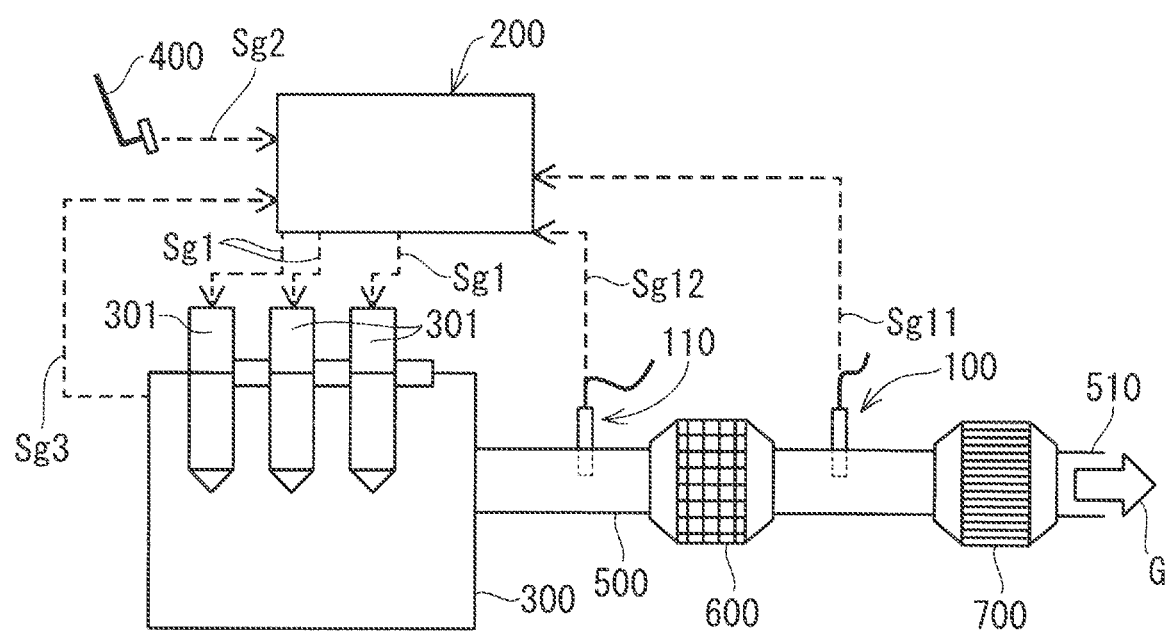
FIG. 1 is a diagram schematically illustrating a schematic configuration of a diesel engine system 1000.

FIG. 1 is a diagram schematically illustrating a configuration of a diesel engine system (hereinafter also simply referred to as engine system) 1000 including a gas sensor 100 as an exemplary execution target of an output degradation reduction process (to be described later in detail) according to the present preferred embodiment.

The engine system 1000 mainly includes the gas sensor 100, a temperature sensor 110, an electronic control unit 200 as a control device configured to control operation of the entire engine system 1000 including the gas sensor 100, an engine main body 300 as an internal combustion, a plurality of fuel injection valves 301 configured to inject fuel into the engine main body 300, a fuel injection instruction unit 400 for instructing the fuel injection valves 301 to perform fuel injection, an exhaust pipe 500 as an exhaust path for externally discharging an exhaust gas (engine exhaust) G generated in the engine main body 300, and an oxidation catalyst 600 such as platinum or palladium provided halfway through the exhaust pipe 500 to oxidize or adsorb any unburned hydrocarbon gas in the exhaust gas G. In the present preferred embodiment, a position closer to the engine main body 300 on one end side of the exhaust pipe 500 is referred to as an upstream side, and a position closer to an outlet 510 provided on a side opposite to the engine main body 300 is referred to as a downstream side.

The engine system 1000 is typically mounted in a vehicle, and in such a case, the fuel injection instruction part 400 is an accelerator pedal.

In the engine system 1000, the electronic control unit 200 issues a fuel injection instruction signal sg1 to the fuel injection valves 301. The fuel injection instruction signal sg1 is usually issued in response to a fuel injection request signal sg2 for demanding an injection of a predetermined amount of fuel, which is provided from the fuel injection instruction part 400 to the electronic control unit 200 during the operation (action) of the engine system 1000 (e.g., an accelerator pedal is depressed so that an optimum fuel injection reflecting a large number of parameters, such as the position of an accelerator, an amount of oxygen intake, an engine speed, and torque is demanded).

A monitor signal sg3 for monitoring various situations inside the engine main body 300 is provided from the engine main body 300 to the electronic control unit 200.

In case that the engine system 1000 is a diesel engine, the exhaust gas G exhausted from the engine main body 300 is a gas in an excessive oxygen ($O_2$) atmosphere having an oxygen concentration of approximately 10%. Specifically, such an exhaust gas G contains oxygen and unburned hydrocarbon gas, and also contains nitrogen oxide, soot (graphite), and the like. In this specification, an unburned hydrocarbon gas is supposed as a gas (target gas) targeted for the adsorption or oxidation process in the oxidation catalyst 600. The unburned hydrocarbon gas contains not only typical hydrocarbon gases (classified as hydrocarbons by a chemical formula) such as $C_2H_4$, $C_3H_6$, and n-C8, but also carbon monoxide (CO). The gas sensor 100 can preferably detect a target gas, including CO. However, $CH_4$ is excluded.

The engine system 1000 may include one or a plurality of purification devices 700 at some midpoint of the exhaust pipe 500, in addition to the oxidation catalyst 600.

The oxidation catalyst 600 is provided to adsorb or oxide an unburned hydrocarbon gas in the exhaust gas G that has flowed from the upstream side to prevent the unburned hydrocarbon gas from flowing out through the exhaust port 510 at the end of the exhaust pipe 500.

The gas sensor 100 is disposed downstream of the oxidation catalyst 600 in the exhaust pipe 500 and detects the concentration of an unburned hydrocarbon gas in the relevant portion. The temperature sensor 110 is disposed upstream of the oxidation catalyst 600 and detects the temperature (exhaust temperature) of the exhaust gas G in the relevant portion. The gas sensor 100 and the temperature sensor 110 are each disposed such that one end thereof is inserted into the exhaust pipe 500.

A detection signal sg11 issued from the gas sensor 100 and an exhaust temperature detection signal sg12 issued from the temperature sensor 110 are provided to the electronic control unit 200. These signals provided to the electronic control unit 200 are used for operation control of the engine system 1000. The example configuration of the gas sensor 100 and the details of diagnosis of degradation will be described below. The temperature sensor 110 may be a conventionally known sensor as one used to measure an exhaust temperature in a common engine system.

The electronic control unit 200 includes storage (not shown) such as memory or HDD, and the storage stores a program for controlling the operations of the engine system 1000, and so on.

FIGS. 2A and 2B are diagrams schematically illustrating the configuration of the sensor element 101 as a main component of the gas sensor 100. FIG. 2A is a vertical sectional view of a sensor element 101, taken along the longitudinal direction thereof. FIG. 2B is a diagram including a cross-section of the sensor element 101 perpendicular to the longitudinal direction thereof at a position A-A' of FIG. 2A.

The gas sensor 100 used in the present embodiment is a so-called mixed-potential gas sensor. Generally speaking, the gas sensor 100 determines the concentration of a gas component, which is a measurement target, of a measurement gas using a potential difference that occurs between a sensing electrode 10, which is provided on the surface of the sensor element 101 mainly made of ceramic that is an oxygen-ion conductive solid electrolyte such as zirconia ($ZrO_2$), and a reference electrode 20, which is provided inside the sensor element 101, due to a difference in the concentration of the gas component between the portions near the electrodes on the basis of the principle of mixed potential.

More specifically, the gas sensor 100 is configured to sense, as a measurement gas, an exhaust gas in an exhaust pipe of an internal combustion such as a diesel engine or a gasoline engine, and preferably determine the concentration of a predetermined gas component in the measurement gas. In the presence of a plurality of unburned hydrocarbon gases in a measurement gas, a potential difference occurring between the sensing electrode 10 and the reference electrode 20 is a value reflecting all the unburned hydrocarbon gases, and thus, a concentration value to be determined is also a total sum of the concentrations of the plurality of unburned hydrocarbon gases.

The sensor element 101 mainly includes a reference gas introduction layer 30, a reference gas introduction space 40, and a surface protective layer 50 in addition to the sensing electrode 10 and the reference electrode 20 described above.

The sensor element 101 has the structure in which six layers, namely, a first solid electrolyte layer 1, a second solid electrolyte layer 2, a third solid electrolyte layer 3, a fourth solid electrolyte layer 4, a fifth solid electrolyte layer 5, and a sixth solid electrolyte layer 6, each formed of an oxygen-ion conductive solid electrolyte, are laminated in the stated order from the bottom side of FIGS. 2A and 2B. The sensor element 101 additionally includes other components mainly between these layers or on an outer peripheral surface of the element. The solid electrolytes constituting these six layers are fully airtight. Such a sensor element 101 is manufactured by, for example, laminating ceramic green sheets corresponding to the individual layers, which have been subjected to a predetermined process and printing of a circuit pattern, and further, by integrating the laminated layers through firing.

However, it is not essential for the gas sensor 100 to include the sensor element 101 as such a laminated body composed of six layers. The sensor element 101 may be provided as a laminated body composed of a larger or smaller number of layers, or may have no laminated structure.

In the following description, for the sake of convenience, the surface located as the upper surface of the sixth solid electrolyte layer 6 in FIGS. 2A and 2B is referred to as a front surface Sa of the sensor element 101, and the surface located as the lower surface of the first solid electrolyte layer 1 in FIGS. 2A and 2B is referred to as a rear surface Sb of the sensor element 101. In the determination of the concentration of the unburned hydrocarbon gas in a measurement gas with the gas sensor 100, a predetermined range starting from a distal end E1 being one end of the sensor element 101, which includes at least the sensing electrode 10, is disposed in a measurement gas atmosphere, and the other portion including a base end E2 opposite the distal end E1 is disposed so as not to be in contact with the measurement gas atmosphere.

The sensing electrode 10 is an electrode for sensing a measurement gas. The sensing electrode 10 is formed as a porous cermet electrode made of Pt containing a predetermined ratio of Au, namely, Pt—Au alloy and zirconia. The sensing electrode 10 is provided in a substantially rectangular shape in plan view at a position closer to the distal end E1 that is one end in the longitudinal direction of the sensor element 101 on the front surface Sa. When used, the gas sensor 100 is disposed so that part of the sensor element 101, which includes at least a place at which the sensing electrode 10 is provided, is exposed in a measurement gas.

The catalytic activity of the sensing electrode 10 against combustion of an unburned hydrocarbon gas is disabled in a predetermined concentration range by preferably determining the composition of the Pt—Au alloy being its constituent material. That is, the combustion reaction of an unburned hydrocarbon gas is prevented or reduced in the sensing electrode 10. In the gas sensor 100, accordingly, the potential of the sensing electrode 10 selectively varies, through electrochemical reaction, with respect to (has correlation with) the unburned hydrocarbon gas, in accordance with its concentration. In other words, the sensing electrode 10 is provided so as to have high dependence of potential on concentration for an unburned hydrocarbon gas while having low dependence of potential on concentration for any other component of the measurement gas.

More specifically, in the sensor element 101 of the gas sensor 100 according to the present preferred embodiment, the potential of the sensing electrode 10 has significant concentration dependency in at least part of a concentration range of, for example, 0 ppmC to 10000 ppmC by preferably determining an Au abundance ratio in the surface of a Pt—Au alloy particle forming the sensing electrode 10. This means that the sensing electrode 10 can excellently detect an unburned hydrocarbon gas in this concentration range. For example, the sensing electrode 10 can excellently detect the unburned hydrocarbon gas in a concentration range of 4000 ppmC or lower when the Au abundance ratio is 0.7 or higher, and the sensing electrode 10 can excellently detect the unburned hydrocarbon gas in a concentration range of 4000 ppmC or higher when the Au abundance ratio is 0.1 or higher and lower than 0.7.

In this specification, the Au abundance ratio means an area ratio of the portion covered with Au to the portion at which Pt is exposed in the surface of the noble metal particle of the sensing electrode 10. In this specification, a Au abundance ratio is calculated from a peak intensity of a peak detected for Au and Pt, obtained using X-ray photoelectron spectroscopy (XPS), by a relative sensitivity coefficient method. The Au abundance ratio is 1 when the area of the portion at which Pt is exposed is equal to the area of the portion covered with Au.

The reference electrode 20 is an electrode having a substantially rectangular shape in plan view, which is provided inside the sensor element 101 and serves as a reference in the determination of the concentration of the measurement gas. The reference electrode 20 is provided as a porous cermet electrode of Pt and zirconia.

It suffices that the reference electrode 20 has a porosity of 10% or more and 30% or less and a thickness of 5 μm or more and 15 μm or less. The plane size of the reference electrode 20 may be smaller than that of the sensing electrode 10 as illustrated in FIGS. 2A and 2B, or may be equal to that of the sensing electrode 10.

The reference gas introduction layer 30 is a layer made of porous alumina, which is provided inside the sensor element 101 to cover the reference electrode 20. The reference gas introduction space 40 is an internal space provided on the base end E2 of the sensor element 101. Air (oxygen), serving as a reference gas in the determination of the concentration of an unburned hydrocarbon gas, is externally introduced into the reference gas introduction space 40.

The reference gas introduction space 40 and the reference gas introduction layer 30 are in communication with each other, and accordingly, in the use of the gas sensor 100, the surrounding of the reference electrode 20 is always filled with air (oxygen) through the reference gas introduction space 40 and the reference gas introduction layer 30. During the use of the gas sensor 100, thus, the reference electrode 20 always has a constant potential.

The reference gas introduction space 40 and the reference gas introduction layer 30 are provided so as not to come into contact with a measurement gas owing to their surrounding solid electrolytes. This prevents the reference electrode 20 from coming into contact with the measurement gas even if the sensing electrode 10 is exposed to the measurement gas.

In the case illustrated in FIG. 2A, the reference gas introduction space 40 is provided in such a manner that part of the fifth solid electrolyte layer 5 is in communication with the exterior on the base end E2 of the sensor element 101. The reference gas introduction layer 30 is provided so as to extend in the longitudinal direction of the sensor element 101 between the fifth solid electrolyte layer 5 and the sixth solid electrolyte layer 6. The reference electrode 20 is provided under the center of gravity of the sensing electrode 10 with reference to FIGS. 2A and 2B.

The surface protective layer 50 is a porous layer made of alumina, which is provided so as to cover at least the sensing electrode 10 on the front surface Sa of the sensor element 101. The surface protective layer 50 is provided as an electrode protective layer that prevents or reduces the degradation of the sensing electrode 10 due to continuous exposure to a measurement gas during the use of the gas sensor 100. In the case illustrated in FIG. 2A, the surface protective layer 50 is provided so as to cover not only the sensing electrode 10 but also substantially the entire front surface Sa of the sensor element 101 except for a predetermined range starting from the distal end E1.

As illustrated in FIG. 2B, the gas sensor 100 is equipped with a potentiometer 60 capable of measuring a potential difference between the sensing electrode 10 and the reference electrode 20. Although FIG. 2B schematically illustrates wiring between the potentiometer 60 and each of the sensing electrode 10 and the reference electrode 20, in an actual sensor element 101, connection terminals (not shown) are provided correspondingly to the respective electrodes on the front surface Sa or the rear surface Sb on the base end E2 side, and wiring patterns (not shown), which connect the respective electrodes and their corresponding connection terminals, are formed on the front surface Sa and inside the element. The sensing electrode 10 and the reference electrode 20 are electrically connected with the potentiometer 60 through the wiring patterns and the connection terminals. Hereinafter, a potential difference between the sensing electrode 10 and the reference electrode 20 is also referred to as a sensor output.

The sensor element 101 further includes a heater part 70, which performs temperature control of heating the sensor element 101 and maintaining the temperature of the sensor element 101, to enhance the oxygen ion conductivity of the solid electrolyte. The heater part 70 includes a heater electrode 71, a heater 72, a through hole 73, a heater insulating layer 74, and a pressure diffusion hole 75.

The heater electrode 71 is an electrode formed while being in contact with the rear surface Sb of the sensor element 101 (in FIGS. 2A and 2B, the lower surface of the first solid electrolyte layer 1). The heater part 70 can be powered externally through the heater electrode 71 connected with an external power supply (not shown).

The heater 72 is an electric resistor provided inside the sensor element 101. The heater 72 is connected with the heater electrode 71 through the through hole 73 and generates heat by being powered externally via the heater electrode 71 to heat the solid electrolytes forming the sensor element 101 and maintain their temperatures.

In the case illustrated in FIGS. 2A and 2B, the heater 72 is buried while being vertically sandwiched between the second solid electrolyte layer 2 and the third solid electrolyte layer 3 so as to extend from the base end E2 to the position below the sensing electrode 10 near the distal end E1. This enables the adjustment of the entire sensor element 101 to the temperature at which the solid electrolytes are activated.

The heater insulating layer 74 is an insulating layer formed of an insulator such as alumina on the upper and lower surfaces of the heater 72. The heater insulating layer 74 is formed for electrical insulation between the second solid electrolyte layer 2 and the heater 72 and for electrical insulation between the third solid electrolyte layer 3 and the heater 72.

The pressure diffusion hole 75 is a part provided to penetrate the third solid electrolyte layer 3 and the fourth electrolyte layer 4 and to be in communication with the reference gas introduction space 40, and is formed to mitigate an internal pressure rise associated with a temperature rise in the heater insulating layer 74.

In the determination of the concentration of an unburned hydrocarbon gas in a measurement gas using the gas sensor 100 having the above configuration, as described above, air (oxygen) is supplied to the reference gas introduction space 40, with the sensor element 101 in only a predetermined range, which starts from the distal end E1 and includes at least the sensing electrode 10, being disposed in a space (in the case illustrated in FIG. 1, the exhaust pipe 500) where the measurement gas exists, and with the sensor element 101 on the base end E2 being isolated from the space. The heater 72 heats the sensor element 101 to 500° C. to 800° C. This heating temperature of the sensor element 101 is referred to as an operating temperature.

In such a state, a potential difference occurs between the sensing electrode 10 exposed to the measurement gas and the reference electrode 20 disposed in the air atmosphere. As described above, however, the potential of the reference electrode 20 disposed in the air (having a constant oxygen concentration) atmosphere is maintained at a constant, whereas the potential of the sensing electrode 10 selectively has a dependence on concentration for the unburned hydrocarbon gas in the measurement gas. The potential difference (sensor output) is thus substantially a value according to the concentration of the measurement gas present around the sensing electrode 10. Therefore, a certain functional relationship (referred to as sensitivity characteristics) holds between the concentration of the unburned hydrocarbon gas and the sensor output. Hereinafter, this sensitivity characteristic is referred to as the sensitivity characteristic of the sensing electrode 10.

In the actual determination of the concentration of the unburned hydrocarbon gas, in advance, a plurality of different mixed gases, each of which has a known concentration of the unburned hydrocarbon gas, are used as the measurement gas, the sensitivity characteristics are experimentally identified by performing a measurement on the sensor output for each measurement gas, and then they are stored in the electronic control unit 200. In the actual use of the gas sensor 100, accordingly, the electronic control unit 200 converts the sensor output, which varies from moment to moment in accordance with the concentration of the unburned hydrocarbon gas in a measurement gas, into the concentration of the target gas component based on the sensitivity characteristics. The concentration of the unburned hydrocarbon gas in the measurement gas can thus be determined almost in real time.

<Output Degradation Reduction Process at Gas Sensor>

The following describes the output degradation reduction process at the gas sensor 100 according to the present preferred embodiment. In the present preferred embodiment, schematically, the output degradation reduction process is a heating process performed on the sensor element 101 of the gas sensor 100 when the gas sensor 100 is started (the gas sensor 100 is driven as preparation for use), in order to prevent output degradation and thus measurement accuracy degradation. In particular, when the gas sensor 100 is provided to the engine system 1000 as illustrated in FIG. 1, the output degradation reduction process is a process performed at cold start of the gas sensor 100. This case is described as an example below.

Figure 3:
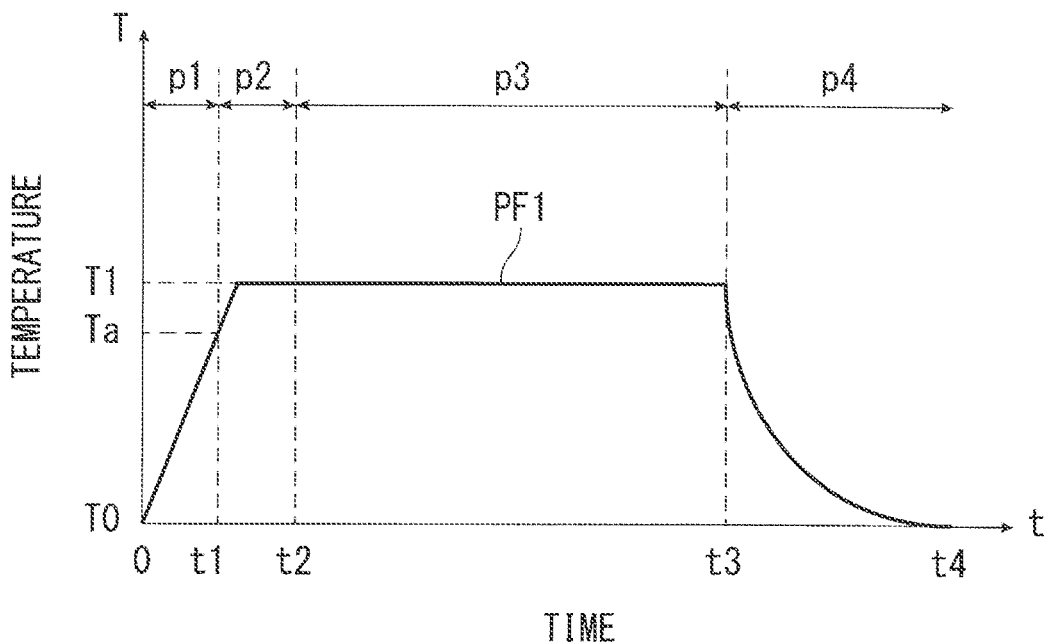
FIG. 3 is a diagram illustrating a temperature profile PF1 of the sensor element 101 of the gas sensor 100 between cold start and stop of the engine system 1000 when an output degradation reduction process is not performed.

First, for comparison, the following describes a case in which the output degradation reduction process is not performed. FIG. 3 is a diagram illustrating a temperature profile PF1 of the sensor element 101 of the gas sensor 100 between cold start ("key on") and stop ("key off") of the engine system 1000 when the output degradation reduction process is not performed.

In FIG. 3, T=T0 is defined as an initial temperature of the sensor element 101, which is typically a temperature (50° C. approximately at highest) near an external air temperature. T=T1 is defined as an operating temperature of the sensor element 101, which is set in advance. T=Ta is defined as an adsorption threshold temperature of the sensor element 101, which is set such that, when the temperature of the sensor element 101 is equal to or higher than the adsorption threshold temperature, no unburned hydrocarbon gas adsorbs to the sensing electrode 10 of the sensor element 101. However, the adsorption threshold temperature Ta does not necessarily need to be specifically specified, and the operating temperature T1 only needs to be set such that T1>Ta reliably holds.

Upon cold start of the engine system 1000 through "key on" at time t=0, the sensor element 101 starts being energized (in other words, the gas sensor 100 including the sensor element 101 is started) and is heated at a predetermined temperature-increase speed from the initial temperature T0 (which is typically a temperature near the external air temperature) to the operating temperature T1 by the heater 72 provided inside the sensor element 101.

On the other hand, exhaust gas is generated from the engine main body 300 of the engine system 1000 after the cold start. For a while after "key on", the exhaust gas has low temperature and the oxidation catalyst 600 is inactive, and thus an unburned hydrocarbon gas contained in the exhaust gas passes through the oxidation catalyst 600 and reaches where the gas sensor 100 is disposed. Thus, the unburned hydrocarbon gas is likely to adsorb to the sensing electrode 10 of the sensor element 101 in period p1 from t=0 to t=t1 at which the sensor element 101 reaches at the adsorption threshold temperature Ta.

However, in a usual case, the sensor element 101 reaches at the operating temperature T1 earlier than the oxidation catalyst 600 is activated. Accordingly, in period p2 from t=t1 to t=t2 at which the oxidation catalyst 600 is activated, the unburned hydrocarbon gas passes through the oxidation catalyst 600 but does not adsorb to the sensing electrode 10 of the sensor element 101.

In period p3 from t=t2 to t=t3 at which "key off" is performed, the oxidation catalyst 600 is activated. Accordingly, the unburned hydrocarbon gas does not pass through the oxidation catalyst 600, and thus does not adsorb to the sensing electrode 10 of the sensor element 101. The period p3 is a period in which the engine system 1000 is in a usual operation state.

When "key off" is performed at time t=t3, the engine main body 300 stops and the heating by the heater 72 maintaining the operating temperature T1 is ended at the sensor element 101. Accordingly, no exhaust gas is newly generated from the engine main body 300, and the temperature of the sensor element 101 abruptly decreases to a temperature lower than the adsorption threshold temperature Ta along with decrease of the temperature of the oxidation catalyst 600. Thus, in period p4 after time t=t3, the unburned hydrocarbon gas in the exhaust gas remaining in the exhaust pipe 500 is likely to adsorb to the sensing electrode 10 of the sensor element 101. Although FIG. 3 illustrates an example in which the temperature of the sensor element 101 returns to the initial temperature T0 at time t=t4 as the end of period p4, a temperature at which the sensor element 101 reaches after "key off" is not necessarily the same as the initial temperature T0.

As described above, when the output degradation reduction process is not performed, the unburned hydrocarbon gas contained in the exhaust gas is likely to adsorb to the sensing electrode 10 of the sensor element 101 at "key on" and "key off". The engine system 1000 is typically used through repetitions of "key on" and "key off", and thus the adsorption of the unburned hydrocarbon gas to the sensing electrode 10 temporally proceeds through long-term use. This progress of the adsorption of the unburned hydrocarbon gas is considered to be a factor of measurement accuracy degradation of the gas sensor 100. A conventional recovery process is performed to solve this temporal adsorption of the unburned hydrocarbon gas at an optional timing.

Figure 4:
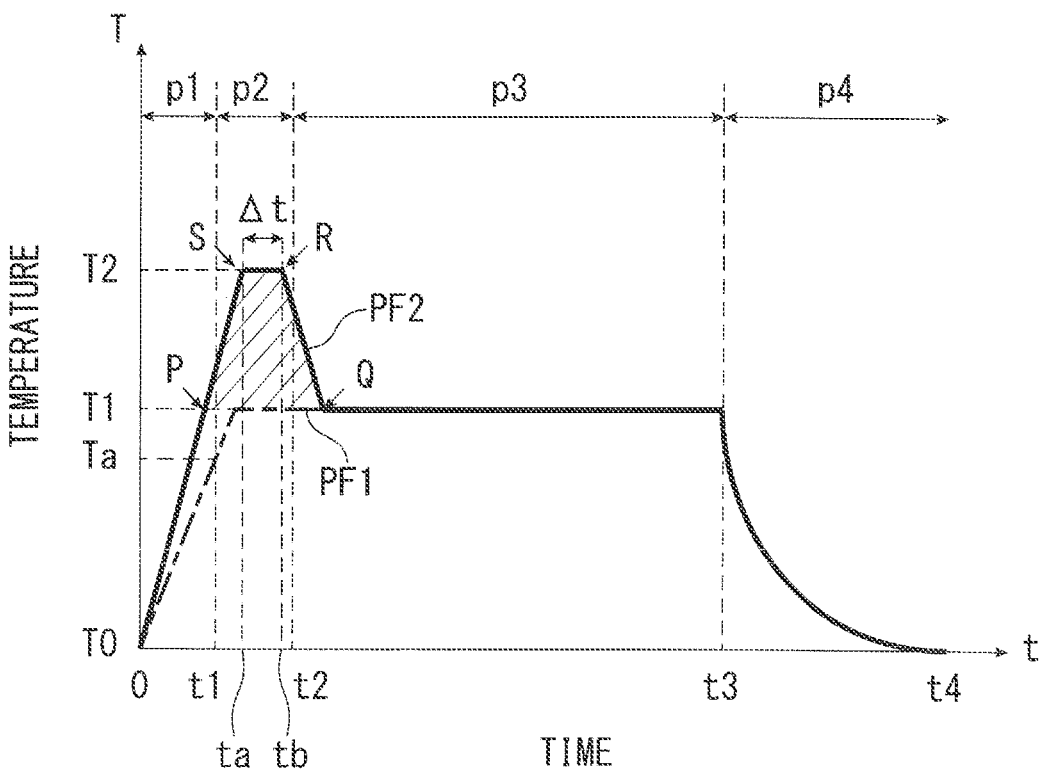
FIG. 4 is a diagram illustrating a temperature profile PF2 of the sensor element 101 of the gas sensor 100 between cold start and stop of an engine main body 300 when the output degradation reduction process is performed.

FIG. 4 is a diagram illustrating a temperature profile PF2 of the sensor element 101 of the gas sensor 100 between cold start and stop of the engine main body 300 when the output degradation reduction process is performed. FIG. 4 also illustrates the temperature profile PF1 and the four periods p1 to p4 for comparison.

Specifically, the output degradation reduction process according to the present preferred embodiment is a process in which the sensor element 101 is temporarily heated to a temperature higher than the operating temperature T1 at start of the gas sensor 100.

Specifically, when "key on" is performed on the engine system 1000 at time t=0, the sensor element 101 is heated by the heater 72 inside the sensor element 101 at the predetermined temperature-increase speed from the initial temperature T0 to a predetermined highest temperature (highest reach temperature) T2.

Preferably, the temperature-increase speed in this case is set to be higher than the temperature-increase speed when the output degradation reduction process is not performed. It is intended to shorten a time until the adsorption threshold temperature Ta is reached, thereby reducing adsorption of an unburned hydrocarbon gas to the sensing electrode 10.

In FIG. 4, time t=ta is later than time t=t1 at which the sensor element 101 reaches at the adsorption threshold temperature Ta when the output degradation reduction process is not performed, but this is not essential.

After having reached at the highest temperature T2 at time t=ta, the sensor element 101 is maintained at the highest temperature T2 for a predetermined time period $\Delta t = tb - ta$ until a predetermined time t=tb, and then decreased to the operating temperature T1. The time period $\Delta t$ is also referred to as a highest-temperature keeping time. The shape of the temperature profile PF2 after the sensor element 101 has reached at the operating temperature is same as that of the temperature profile PF1.

As in this case, when the sensor element 101 is heated to the temperature higher than the operating temperature T1 as the output degradation reduction process at start of each use of the gas sensor 100, any unburned hydrocarbon gas, which is adsorbed to the sensing electrode 10 through the period in which the sensor element 101 at the initial temperature T0 reaches at the adsorption threshold temperature Ta and the period after "key off" at previous use, is removed by desorption or oxidation through the output degradation reduction process. Thus, the gas sensor 100 can be used while output degradation attributable to adsorption of the unburned hydrocarbon gas is excellently reduced. This means that the concentration of a measurement target component can be measured constantly at an excellent accuracy.

In other words, it can be said that, in the output degradation reduction process, a process corresponding to a conventional thermal process, which has been performed to recover the output of the gas sensor 100 degraded through continuous use, is performed, at start of each use of the gas sensor 100. When the output degradation reduction process is performed in this manner, the progress of adhesion of an unburned hydrocarbon gas to the sensing electrode 10 is reduced. This eliminates the need to perform the conventionally performed recovery process.

The conventional recovery process is to be performed during a steady operation of the engine system 1000, and thus the gas sensor 100 cannot be used during the recovery process. However, since the output degradation reduction process according to the present preferred embodiment is to be performed at a timing when the oxidation catalyst 600 is inactive, the unavailability of the gas sensor 100 due to the recovery process never occurs during the steady operation of the engine system 1000.

In FIG. 4, time t=tb is earlier than time t=t2 at which the oxidation catalyst 600 is activated, and the sensor element 101 reaches at the operating temperature T1 later than time t=t2, but these are not essential.

The highest-temperature keeping time period Δt=tb−ta may be zero. Specifically, the temperature of the sensor element 101 may be decreased to the operating temperature T1 right after having reached at the highest temperature T2 at time t=ta. Naturally, in this case, ta=tb.

The output degradation reduction process provides a larger effect when the highest temperature T2 is higher than the operating temperature T1 by a larger amount and a treatment time (in particular, the highest-temperature keeping time period Δt) is longer. However, a specific upper limit of the highest temperature T2 varies with, for example, the material of the sensing electrode 10. As described above, when the sensing electrode 10 contains Pt—Au alloy, the highest temperature T2 is preferably set to 850° C. or lower. It is not preferable that the highest temperature T2 is higher than 850° C. because, for example, evaporation of Au as constituent material potentially causes property change, deform, damage, and the like to the sensing electrode 10. It is also not preferable that the highest-temperature keeping time period Δt is set to be unnecessarily long because the gas sensor 100 is maintained in an unmeasurable state in spite that the oxidation catalyst 600 is activated.

The time integral value (in the unit of ° C.·sec) of a difference between a temperature T and the operating temperature T1 in a range in which the temperature is higher than the operating temperature T1 in the temperature profile PF2 can be used as an index (performance evaluation value) evaluating the performance of the output degradation reduction process under various kinds of conditions. In the case illustrated in FIG. 4, the area value of a hatched quadrilateral region PQSR corresponds to the performance evaluation value. The inventor of the present invention has confirmed that the output degradation of the gas sensor 100 is more effectively reduced at a larger performance evaluation value.

For example, a threshold (sensor output threshold) of an allowable value of the sensor output is specified as a ratio relative to the absolute value of the sensor output or an initial output value in advance. In addition, a minimum value of the performance evaluation value, which is determined in a condition range of the output degradation reduction process in which the sensor output higher than the sensor output threshold is enabled, is specified as a threshold of the performance evaluation value in advance. Accordingly, the output degradation attributable to adhesion of an unburned hydrocarbon gas to the sensing electrode 10 can be reliably reduced as long as the output degradation reduction process is performed under such a condition that the performance evaluation value exceeding the threshold is provided. A specific threshold of the performance evaluation value varies with the individual gas sensor 100.

As described above, according to the present preferred embodiment, temporal output degradation of the gas sensor, which would otherwise occur due to adsorption of an unburned hydrocarbon gas to the electrode, can be excellently reduced without an unavailable time of the gas sensor by performing, at start of the gas sensor, the output degradation reduction process of heating the sensor element to the temperature higher than the operating temperature.

<Modifications>

The above preferred embodiment exemplarily describes a mixed-potential type gas sensor whose measurement target component is hydrocarbon gas, but application of the output degradation reduction process according to the above-described preferred embodiment is not limited thereto. The same effect can be obtained when the output degradation reduction process is applied to a mixed-potential type gas sensor whose measurement target component is another type of gas, and also to another gas sensor (for example, an oxygen sensor) that is driven at relatively low temperature (for example, 600° C. or lower) and in which a gas component adsorbs to the electrode.

EXAMPLES

The engine system 1000 including a diesel engine having a displacement of 3L was used as the engine main body 300 to evaluate a relation between the condition of the output degradation reduction process and the degree of output degradation reduction of the gas sensor 100.

Specifically, such an operation cycle was repeated that the engine system 1000 was operated under a predetermined condition for 30 minutes after cold start and then stopped, and thereafter was cooled to an external air temperature while being left to stand for 24 hours. This operation cycle was repeated until the third cycle thereof ends. The output degradation reduction process was performed at the gas sensor 100 at cold start in the second and third cycles. The output degradation reduction process was performed under 10 different conditions (No. 1 to 10) including a case in which the process was not performed. Then, the degree (degradation reduction degree) of output degradation reduction achieved by the output degradation reduction process was judged from the degree of difference in output change at operation in each cycle. The operating temperature T1 of the sensor element 101 was set to 500° C.

More specifically, in the case that the output degradation reduction process was performed, a temperature-increase speed from the initial temperature T0 to the highest temperature T2 and a temperature-decrease speed from the highest temperature T2 to the operating temperature T1 were both set to 13.6° C./sec, the highest temperature T2 was set to three different levels of 850° C., 750° C., and 650° C., and the highest-temperature keeping time period Δt was set to three different levels of 0 sec, 30 sec, of 60 sec. In other words, the output degradation reduction process was performed under the nine different conditions. A temperature-increase speed from the initial temperature T0 to the operating temperature T1 was set to 10.5° C./sec when the output degradation reduction process is not performed.

Figure 5:
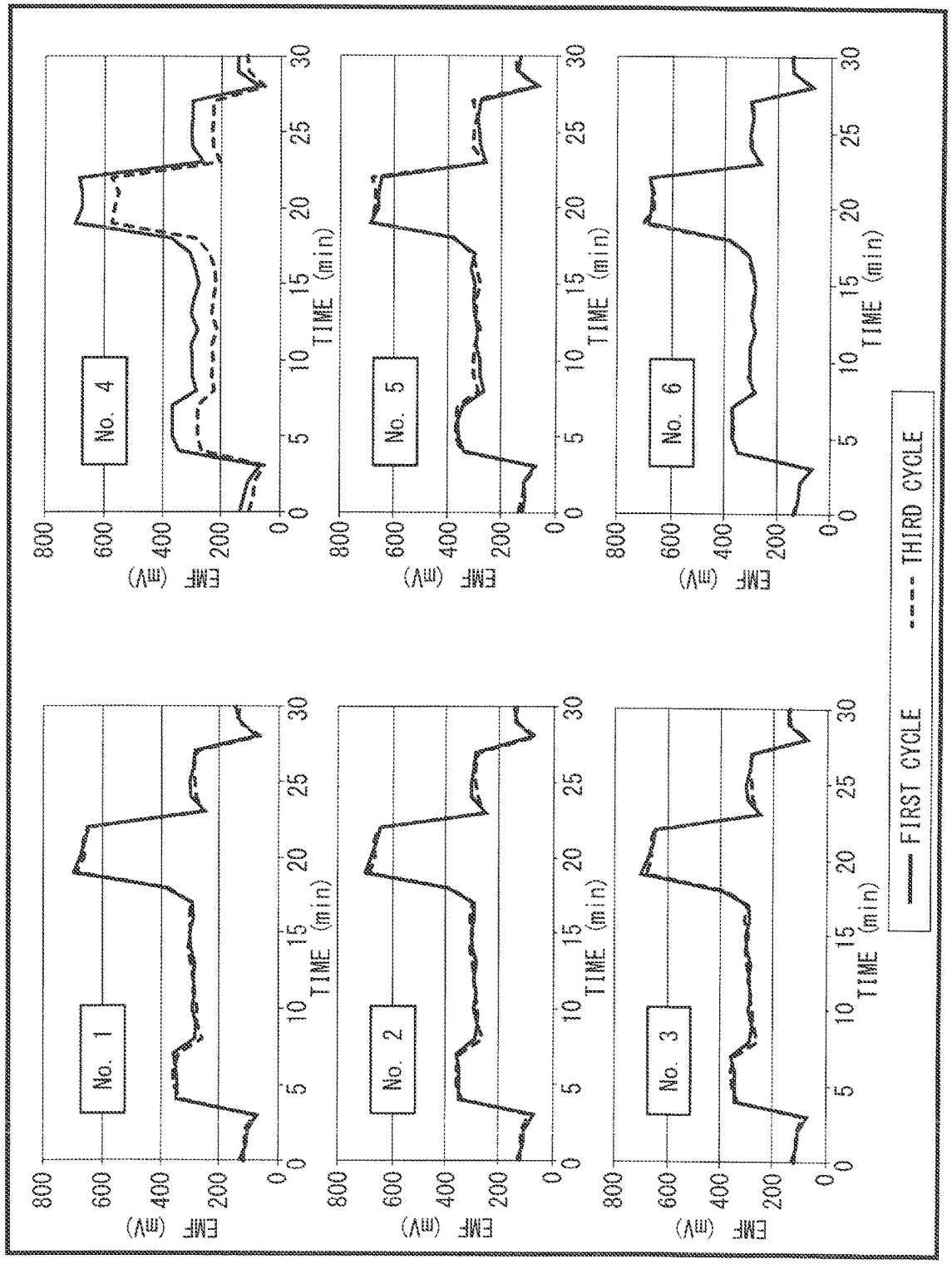
FIG. 5 is a diagram illustrating temporal change of a sensor output at operation in the first and third cycles for output degradation reduction process conditions No. 1 to 6.
Figure 6:
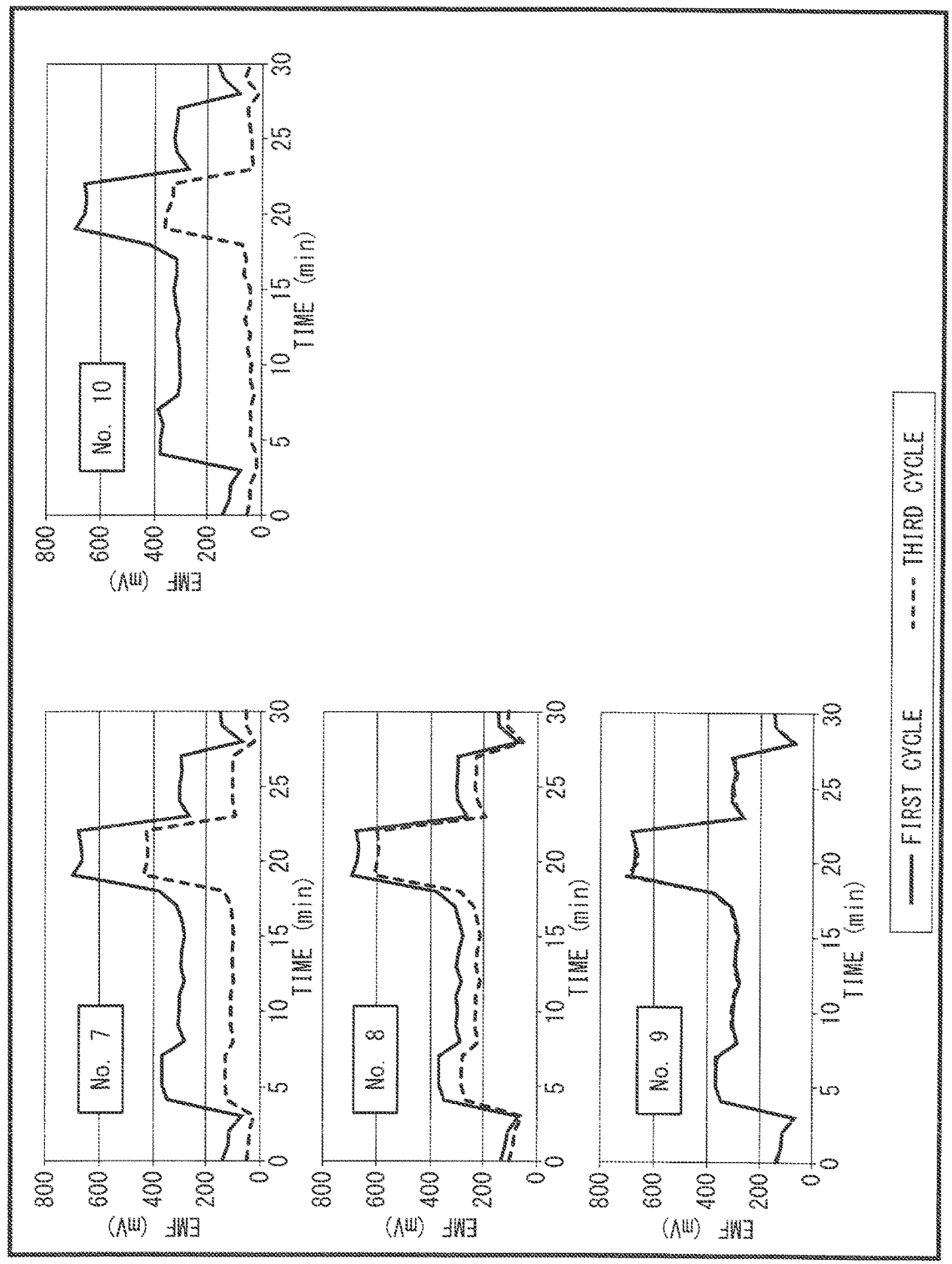
FIG. 6 is a diagram illustrating temporal change of the sensor output at operation in the first and third cycles for output degradation reduction process conditions No. 7 to 10.

Table 1 lists the highest temperature T2, the highest-temperature keeping time period Δt, the performance evaluation value (the process performance evaluation value), and results of judgment of the degradation reduction degree for the output degradation reduction process under the 10 conditions (No. 1 to 10). FIGS. 5 and 6 are diagrams of temporal change of the sensor output at operation in the first and third cycles for the output degradation reduction process conditions No. 1 to 10. The former illustrates results for the conditions No. 1 to 6, and the latter illustrates results for the conditions No. 7 to 10.

TABLE 1

| NO. | HIGHEST TEMPERATURE T2 (° C.) | HIGHEST-TEMPERATURE KEEPING TIME PERIOD Δt (sec) | PROCESS PERFORMANCE EVALUATION VALUE (° C. · sec) | DEGRADATION REDUCTION DEGREE JUDGEMENT |
|---|---|---|---|---|
| 1 | 850 | 0 | 9007 | ○ |
| 2 | 850 | 30 | 19507 | ○ |
| 3 | 850 | 60 | 30007 | ○ |
| 4 | 750 | 0 | 4596 | Δ |
| 5 | 750 | 30 | 12096 | ○ |
| 6 | 750 | 60 | 19596 | ○ |
| 7 | 650 | 0 | 1655 | × |
| 8 | 650 | 30 | 6155 | Δ |
| 9 | 650 | 60 | 10655 | ○ |
| 10 | WITHOUT PROCESS | WITHOUT PROCESS | WITHOUT PROCESS | × |

The degradation reduction degree was judged based on the temporal change of the sensor output at operation in the first and third cycles illustrated in FIGS. 5 and 6. Specifically, it is judged that the output degradation was sufficiently reduced when a sensor output value in the third cycle is 80% of the sensor output value in the first cycle or higher during 30-minute operation. In Table 1, a circle denotes an output degradation reduction process condition under which such a judgement result was obtained. It is judged that the output degradation was reduced to some extent when the sensor output value in the third cycle is equal to or higher than 70% and lower than 80% of the sensor output value in the first cycle. In Table 1, a triangle denotes an output degradation reduction process condition under which such a judgement result was obtained. It is judged that the output degradation was not reduced when the sensor output value in the third cycle is lower than 70% of the sensor output value in the first cycle. In Table 1, a cross denotes an output degradation reduction process condition under which such a judgement result was obtained.

Table 1 and FIGS. 5 and 6 indicate that the output degradation tends to be more reduced by the output degradation reduction process with the short highest-temperature keeping time period Δt as the highest temperature T2 is higher. This means that the highest-temperature keeping time period Δt can be shortened as long as the performance evaluation value is maintained by increasing the highest temperature T2.

Specifically, in the output degradation reduction process under the conditions No. 7 to 9 in which the highest temperature T2 was set to 650° C., the output degradation was sufficiently reduced only under the condition No. 9 in which the highest-temperature keeping time period Δt was set to 60 sec. However, in the output degradation reduction process under the conditions No. 1 to 3 in which the highest temperature T2 was set to 850° C., the output degradation was reduced even under the condition No. 1 in which the highest-temperature keeping time period Δt was set to 0 sec.

There is a correlation between the performance evaluation value and the degradation reduction degree. Specifically, for the output degradation reduction process conditions (No. 1, 2, 3, 5, 6, and 9) each denoted by a circle in the column of degradation reduction degree in Table 1, the performance evaluation value was 9000° C.·sec or higher. In fact, as illustrated in FIGS. 5 and 6, the sensor output had almost no difference between the first and third cycles. The same result was obtained for the sensor output in the second cycle, which is not illustrated.

For the output degradation reduction process conditions (No. 4 and 8) each denoted by a triangle in the column of degradation reduction degree in Table 1, the performance evaluation value was 4596° C.·sec and 6155° C.·sec, respectively, which is smaller than 9000° C.·sec. The sensor output in the second cycle, which is not illustrated, was approximately at the middle of the sensor outputs in the first and third cycles.

For the output degradation reduction process condition (No. 7) denoted by a cross in the column of degradation reduction degree, the performance evaluation value was only 1655° C.·sec approximately. The sensor output in the third cycle had a profile shape similar to that for the condition No. 10 in which the output degradation reduction process was not performed.

The above-described results indicate that at least the degradation of the gas sensor 100 attributable to adhesion of an unburned hydrocarbon gas can be reduced as long as the output degradation reduction process is performed under a condition in which the performance evaluation value is sufficiently high.

While the invention has been shown and described in detail, the foregoing description is in all aspects illustrative and not restrictive. It is therefore understood that numerous modifications and variations can be devised without departing from the scope of the invention.

What is claimed is:

1. A method of reducing output degradation of a gas sensor, said gas sensor including:
    a sensor element made of an oxygen-ion conductive solid electrolyte;
    at least one electrode provided to said sensor element so as to contact a measurement gas having a gas component that adsorbs to the at least one electrode and that degrades an output of the gas sensor;
    a heater provided to said sensor element and configured to heat said sensor element; and
    a controller configured to control said gas sensor, said gas sensor being a mixed-potential type gas sensor,
    said method comprising the steps of:
    a) at start of said gas sensor, by said heater, raising a temperature of said sensor element from an initial temperature being a non-operating temperature, and further heating said sensor element to a predetermined temperature higher than an operating temperature for a predetermined time period to desorb the gas component that adsorbs to the at least one electrode at a start of said gas sensor to reduce output degradation of the gas sensor;

b) decreasing, to said operating temperature, the temperature of said sensor element heated to the temperature higher than said operating temperature; and determining a performance evaluation value of output degradation reduction of said gas sensor that is defined as a time integral value of a difference between the temperature of said sensor element and said operating temperature over a range in which the temperature of said sensor element is heated in said heating step to said predetermined temperature higher than said operating temperature, wherein in said step a), at start of said gas sensor, said heater heats said sensor element at said predetermined temperature for said predetermined time period so that said performance evaluation value exceeds a threshold value set in advance based on an output degradation allowable range of said gas sensor.

2. The method of reducing output degradation of a gas sensor according to claim 1, wherein said gas sensor includes, as said at least one electrode, a sensing electrode, and wherein a catalytic activity of said sensing electrode is disabled against a predetermined measurement gas component in said measurement gas;

said gas sensor further includes a reference electrode provided so as to contact a predetermined reference gas, and said gas sensor measures a concentration of said predetermined measurement gas component based on a potential difference that occurs between said sensing electrode and said reference electrode.

3. The method of reducing output degradation of a gas sensor according to claim 2, wherein said predetermined measurement gas component includes hydrocarbon and carbon monoxide, said sensing electrode is made of Pt—Au alloy, and in said step a), at start of said gas sensor, said heater heats said sensor element to 850° C. or lower as said predetermined temperature higher than said operating temperature.

* * * * *